United States Patent
Dai et al.

(10) Patent No.: US 10,551,302 B2
(45) Date of Patent: Feb. 4, 2020

(54) CALIBRATION OF OPTICAL COMPUTING DEVICES USING TRACEABLE FILTERS

(71) Applicant: Halliburton Energy Services, Inc., Houston, TX (US)

(72) Inventors: Bin Dai, Spring, TX (US); Christopher Jones, Houston, TX (US); Darren Gascooke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/741,712

(22) PCT Filed: Aug. 13, 2015

(86) PCT No.: PCT/US2015/045076
§ 371 (c)(1),
(2) Date: Jan. 3, 2018

(87) PCT Pub. No.: WO2017/027040
PCT Pub. Date: Feb. 16, 2017

(65) Prior Publication Data
US 2018/0195955 A1    Jul. 12, 2018

(51) Int. Cl.
| | |
|---|---|
| *G01N 21/25* | (2006.01) |
| *G01N 21/27* | (2006.01) |
| *E21B 49/08* | (2006.01) |
| *E21B 47/06* | (2012.01) |
| *E21B 47/12* | (2012.01) |
| *E21B 49/00* | (2006.01) |

(52) U.S. Cl.
CPC ......... *G01N 21/274* (2013.01); *E21B 49/082* (2013.01); *G01N 21/255* (2013.01); *E21B 47/065* (2013.01); *E21B 47/12* (2013.01); *E21B 49/00* (2013.01); *G01N 2201/13* (2013.01)

(58) Field of Classification Search
CPC ........ G01J 3/26; G01J 3/02; G01J 3/51; G01J 9/00; G01N 21/255
USPC .......................................................... 356/416
See application file for complete search history.

(56) References Cited

U.S. PATENT DOCUMENTS

| | | | |
|---|---|---|---|
| 6,690,817 B1 * | 2/2004 | Cabib ................ | G01B 11/0675 382/134 |
| 9,632,013 B2 * | 4/2017 | Rivas ....................... | G01N 1/10 |
| 2003/0026762 A1 * | 2/2003 | Malmros .............. | A61B 5/0059 424/9.6 |
| 2009/0316150 A1 | 12/2009 | Myrick et al. | |

(Continued)

FOREIGN PATENT DOCUMENTS

| | | |
|---|---|---|
| JP | 2000206037 A | 7/2000 |
| JP | 2007232733 A | 9/2007 |

(Continued)

OTHER PUBLICATIONS

International Search Report and the Written Opinion of the International Search Authority, or the Declaration, dated Apr. 14, 2016, PCT/US2015/045076, 16 pages, ISA/KR.

*Primary Examiner* — Md M Rahman
(74) *Attorney, Agent, or Firm* — Haynes and Boone, LLP

(57) ABSTRACT

Calibration of optical computing devices is achieved using mapping functions that map real detector responses to simulated detector responses which are simulated using high-resolution spectra of traceable optical filters and optical computing device characteristics.

26 Claims, 5 Drawing Sheets

(56) References Cited

U.S. PATENT DOCUMENTS

| | | | |
|---|---|---|---|
| 2010/0042348 A1 | 2/2010 | Bakker | |
| 2013/0042673 A1* | 2/2013 | Saari-Nordhaus | G01N 30/82 73/61.55 |
| 2013/0044200 A1* | 2/2013 | Brill | G02B 21/365 348/79 |
| 2013/0162999 A1 | 6/2013 | Myrick et al. | |
| 2013/0284901 A1* | 10/2013 | Freese | G01N 21/17 250/208.2 |
| 2014/0020462 A1* | 1/2014 | Irani | G01N 33/2823 73/152.55 |
| 2015/0100244 A1* | 4/2015 | Hannum | G16B 20/00 702/19 |
| 2015/0116721 A1* | 4/2015 | Kats | G01J 3/26 356/454 |
| 2015/0369664 A1* | 12/2015 | Garsha | G01J 3/10 356/402 |
| 2016/0202181 A1* | 7/2016 | Freese | G01N 21/59 356/434 |
| 2016/0252449 A1* | 9/2016 | Price | G01N 21/21 356/364 |
| 2016/0331230 A1* | 11/2016 | Liu | A61B 3/135 |
| 2016/0349400 A1* | 12/2016 | Chen | G01V 8/02 |
| 2017/0023482 A1* | 1/2017 | Cicerone | G01N 21/65 |
| 2017/0026588 A1* | 1/2017 | Kester | G06K 9/22 |
| 2017/0191939 A1* | 7/2017 | Carriere | G01N 21/65 |
| 2018/0003558 A1* | 1/2018 | Goldring | G01J 3/0291 |

FOREIGN PATENT DOCUMENTS

| | | |
|---|---|---|
| WO | WO 2014/042642 A1 | 3/2014 |
| WO | WO 2015/047238 A1 | 4/2015 |

* cited by examiner

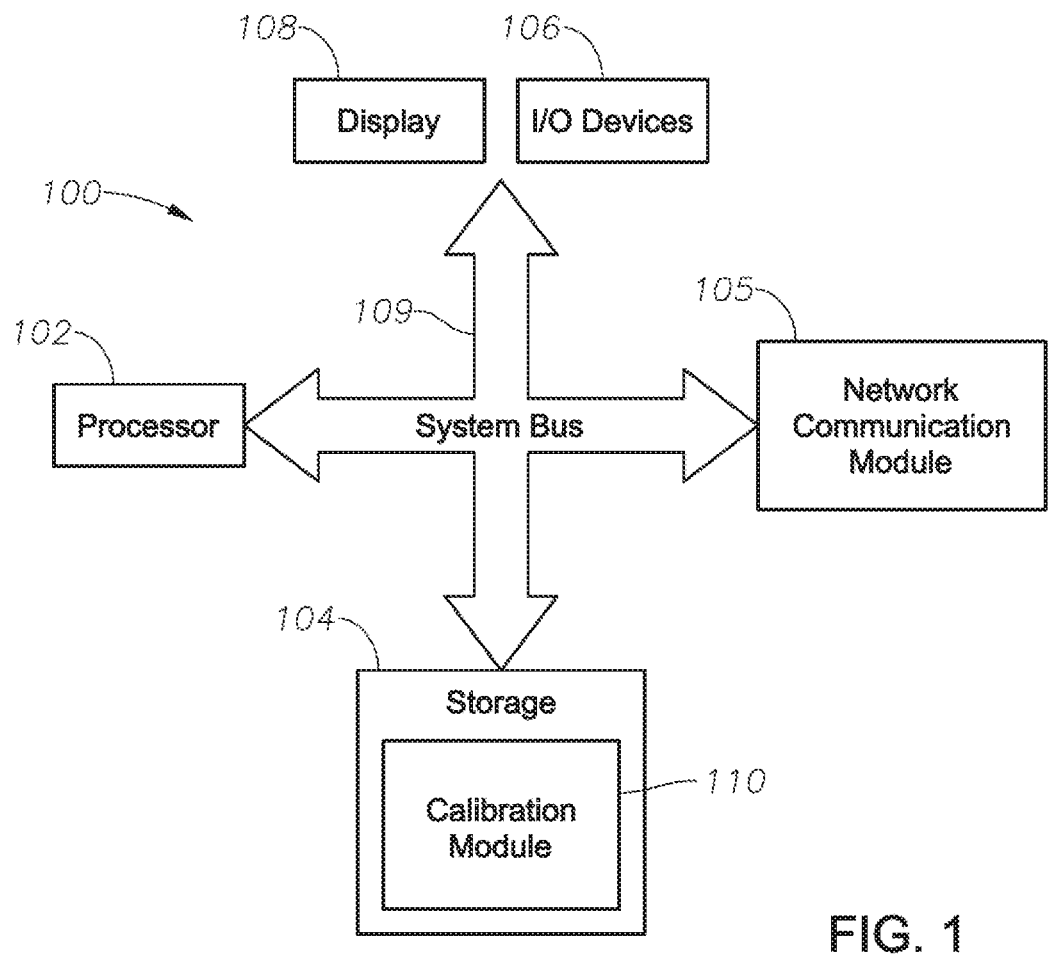
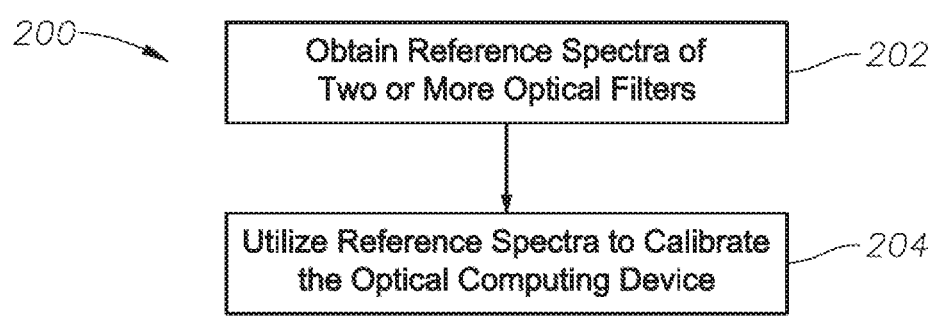

CALIBRATION OF OPTICAL COMPUTING DEVICES USING TRACEABLE FILTERS

PRIORITY

The present application is a U.S. National Stage patent application of International Patent Application No. PCT/US2015/045076, filed on Aug. 13, 2015, the benefit of which is claimed and the disclosure of which is incorporated herein by reference in its entirety.

FIELD OF THE DISCLOSURE

The present disclosure relates generally to optical computing devices and, more specifically, to calibration of optical computing devices using traceable optical filters.

BACKGROUND

Various optical computing techniques have been developed for applications in the Oil and Gas industry. An example of an optical computing device is a device configured to receive an input of electromagnetic radiation from a substance or sample of the substance and produce an output of electromagnetic radiation from a processing element. The processing element may be, for example, an Integrated Computational Element ("ICE") structure. Some optical computing devices utilize optical elements to perform calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. This information is often referred to as the substance's spectral "fingerprint." Thus, the optical computing device, through use of the ICE structure, is capable of extracting the information of the spectral fingerprint of multiple characteristics or analytes within a substance and converting that information into a detectable output regarding the overall properties of a sample.

BRIEF DESCRIPTION OF THE DRAWINGS

FIG. 1 is a block diagram of an optical computing device calibration system according to an illustrative embodiment of the present disclosure;

FIG. 2 is a flow chart of an illustrative calibration method of the present disclosure;

DESCRIPTION OF ILLUSTRATIVE EMBODIMENTS

Figure 3:
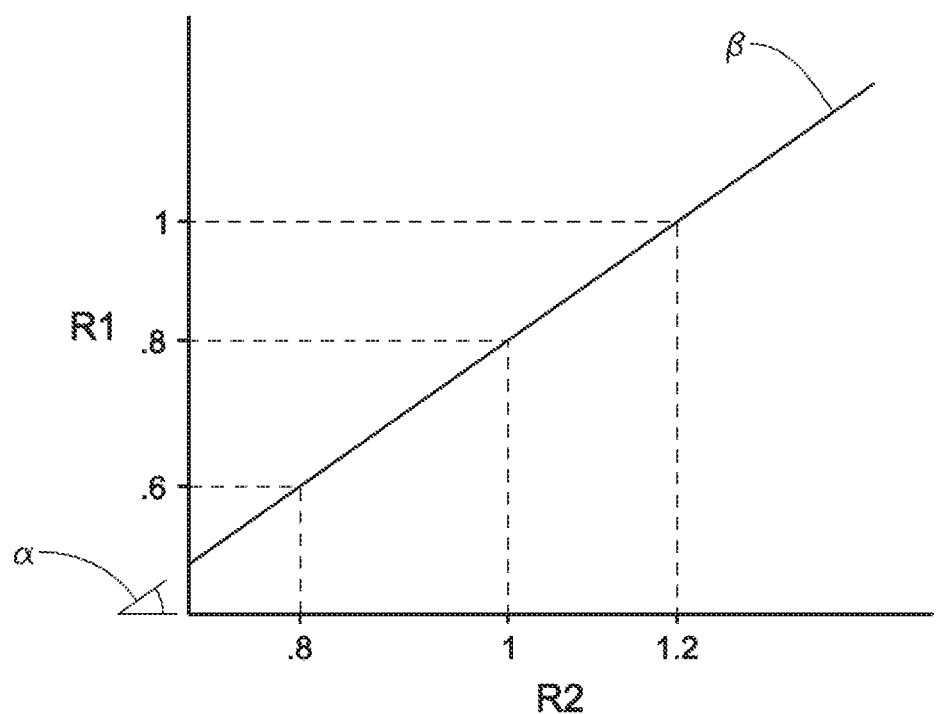
FIG. 3 shows an illustrative mapping function of real detector response ("R2") and simulated detector response ("R1") and a corresponding plot useful to illustrative the mapping principle.

Illustrative embodiments and related methods of the present disclosure are described below as they might be employed in a calibration model for optical computing devices. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Further aspects and advantages of the various embodiments and related methods of the disclosure will become apparent from consideration of the following description and drawings.

During operation of optical computing device, the intensity of the light emitted from the light source may fluctuate. Such fluctuations might occur for a variety of reasons, including weakening of the bulb over time or simply due to the absorption characteristics of the sample of interest. As a result, this fluctuation, and its effect on the output signal ratio necessary to accurately calculate the sample characteristic, introduces errors into the output signals and resulting measurements.

In addition, downhole temperature fluctuations can also have a detrimental effect on the accuracy of the optical computing device. As the temperature of the optical computing device changes, the operating characteristics of various components, such as the detectors, are gradually altered as well. As the detector continues to warm, eventually the output signal goes to zero. This phenomenon is referred to as "thermal drift." Since the accuracy of the optical computing device is in-part based upon the stability of the detectors, thermal drift naturally introduces errors into the output signals as well.

To address these issues, conventional methods use calibration models developed using real fluid samples, which is very cost prohibitive and time costly. Use of real fluid samples to calibrate the computing devices requires manipulation of temperatures and pressures, as well as time consuming clean-up procedures, which may take days or weeks to complete. Accordingly, there is a need in the art for a more economically efficient calibration model.

In view of the foregoing, illustrative embodiments and methods of the present disclosure are directed to calibration models for optical computing devices using traceable filters. To achieve this, a mapping function is generated which maps real detector responses to simulated detector responses that are simulated using high-resolution spectra of traceable filters and computing device characteristics (e.g., light source emission profile, filter wheel spectra, detector response profiles). As defined herein, "traceable filters" are optical filters whose spectral output (or reference spectra) is known using, for example, a laboratory spectrometer. In a generalized embodiment, the present disclosure provides models for calibrating detector response outputs of optical computing devices by using two or more traceable optical filters to generate a mapping function between simulated and real detector responses. Once the mapping function is generated, the real detector responses acquired during operation of the computing device can be calibrated to the simulated responses using the mapping function. Thereafter, the calibrated detector output is used to determine the sample characteristic of interest.

More specifically, the present disclosure allows the spectral output of an optical computing device to be calibrated to correct for the difference between real optical detector response outputs and simulated optical detector response outputs. The illustrative methods described here use a set of traceable optical filter standards (e.g., neutral density filters, glass standards, etc.) to attenuate real detector outputs to therefore allow mapping of the real detector responses to simulated detector responses, without using any fluid samples. Because the traceable optical filters may be built-in into the optical sensor, the calibration process can be carried out anytime in the future to re-standardize the computing device if the case of thermal drift.

Although described herein in relation to optical computing devices, the illustrate methods/embodiments described herein are applicable to any spectroscopic sensor that makes quantitatively accurate transmission/absorbance measurements of samples to predict physical or chemical properties of interest (e.g., particle size, density, chemical composition, etc.).

In view of the foregoing, FIG. 1 shows a block diagram of an optical computing device calibration system according to an illustrative embodiment of the present disclosure. As will be described herein, calibration system 100 provides a platform for generating mapping functions used to calibrate optical computing devices using simulated spectral data of traceable filters. After the mapping functions have been generated, the optical computing device may then be calibrated in real-time as desired. Thus, as described herein, the present disclosure provides an efficient method by which to calibrate an optical computing device at any time.

Referring to FIG. 1, calibration system 100 includes at least one processor 102, a non-transitory, computer-readable storage 104, transceiver/network communication module 105, optional I/O devices 106, and an optional display 108 (e.g., user interface), all interconnected via a system bus 109. In one embodiment, the network communication module 105 is a network interface card (NIC) and communicates using the Ethernet protocol. In other embodiment, the network communication module 105 may be another type of communication interface such as a fiber optic interface and may communicate using a number of different communication protocols. Software instructions executable by the processor 102 for implementing software instructions stored within calibration module 110 in accordance with the illustrative embodiments described herein, may be stored in storage 104 or some other computer-readable medium.

Although not explicitly shown in FIG. 1, it will be recognized that calibration system 100 may be connected to one or more public (e.g., the Internet) and/or private networks via one or more appropriate network connections. It will also be recognized that the software instructions comprising calibration module 110 may also be loaded into storage 104 from a CD-ROM or other appropriate storage media via wired or wireless methods.

Moreover, methods and embodiments of this disclosure may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present disclosure. The methods and embodiments of this disclosure may be practiced in distributed-computing environments where tasks are performed by remote-processing devices that are linked through a communications network. In a distributed-computing environment, program modules may be located in both local and remote computer-storage media including memory storage devices. The present disclosure may therefore, be implemented in connection with various hardware, software or a combination thereof in a computer system or other processing system.

The calibration of a sensor to analytes of interest (e.g., C1, C2 or C3, in crude oil, etc.) of samples consists of a two part process: in the first step, calibration models are built which correlate simulated detector responses to analytes of interest (the detail of the simulation and calibration are described below). In the second step, a calibration mapping function of real sensor detector responses to simulated detector responses is developed which allows the calibration model (built in the first step of the process) to be applied on a real sensor.

In step 1, to begin the calibration process, an optical computing device is designed and fabricated. As will be understood by those ordinarily skilled in the art having the benefit of this disclosure, the design process in general involves measuring a sufficient number of fluid samples using, for example, a laboratory spectrometer system (e.g., Fourier transform near infrared spectrometer (FT-NIR), dispersive NIR spectrometer, etc.) to record the spectra data of samples at various temperatures and pressures in a PVT laboratory, for example. The outcome of the design process is an ICE structure that has an optimal spectral profile to allow the analyte of interest to be correlate best with detector response. Next, an optical computing device is fabricated, the spectral profile of the ICE structure is measured using a spectrometer, and the light source emission and detector spectral response profiles are characterized. In additional to the spectral data of each component of the optical sensor, a large number of FTIR spectra of fluid samples are also acquired in a PVT system using the FTIR spectrometer. Thereafter, using the spectral data of the fluid samples and the spectroscopic characterization of the optical computing device, the optical responses of each sample can be estimated by:

$$S = \text{FldSpec} \cdot \text{Conv\_filter\_Trs}, \quad \text{Eq.(1)},$$

where, $$\text{Conv\_filter\_Trs} = (\text{Source\_emission})(\text{Filter\_spec})(\text{Detector\_resp}) \quad \text{Eq.(2)}.$$

S represents integrated detector response outputs of n optical channels on m fluid samples; Fldspec are m FTNIR transmission spectra of fluid samples; the detector outputs/responses S are the dot product of sample transmission spectra and convoluted transmission spectra of optical channels; and Conv_filter_Trs are convoluted transmission spectra of n optical channels. The convoluted transmission spectra are based on the light source emission profile (Source_emission), transmission spectra of ICE structures (Filter_spec), and the detector spectral response curve (Detector_resp).

Thereafter, a multivariate calibration model is developed based on the simulated detector responses S on training samples and properties of interest (e.g., concentration, density, etc). The multivariate calibration model is developed to establish a correlation between simulated detector response S to the concentration of the analyte of interest. These multivariate calibration models can be generated through various statistical and machine learning algorithms, such as, for example, Principal component regression (PCR), Partial least squares regression (PLSR), Multiple linear regression (MLR), Ridge regression (RR), Artificial neural network (ANN), Least Absolute Shrinkage and Selection Operator (LASSO), or support vector machine (SVM).

In step 2, the spectra of two or more traceable filters are acquired and their simulated sensor detector responses ("R1") are calculated according to Equation 3. Also, these traceable filters are then used in the sensor to acquire the real detector responses (R2), then a mapping function is generated to map the relationship between simulated detector responses and real detector responses.

In view of the foregoing, FIG. 2 is a flow chart of an illustrative calibration method of the present disclosure. At block 202, reference spectra of two or more traceable optical filters, such as, for example, neutral density filters or glass, are obtained. The reference spectra may be obtained using, for example, a laboratory spectroscopic instrument (e.g., FT-NIR). As a result, the reference spectra are known (i.e., traceable). The traceable optical filters have different spectral transmission levels because at least two different detector response need to be obtained to allow the mapping function to be developed. Although a fluid sample is not being measured here, the reference spectra each have a defined spectral pattern that simulates the spectral data of a real fluid sample. In other words, the traceable filters work like fluid samples so the traceable reference spectra are treated as fluid sample spectra, simulated detector responses ("R1") for these traceable optical filters are then obtained as described above:

$$R1 = \text{Filter\_Spec} \cdot \text{Conv\_filter\_Trs}, \quad \text{Eq.(3)},$$

where, in this case, Filter_Spec represents the reference spectra of the traceable optical filters.

Next, real detector responses of the traceable optical filters are obtained using, for example a moveable assembly upon which the traceable optical filters are positioned. The moveable assembly may, for example, a rotating carousel or linear array forming part of the optical computing device. Alternatively, the moveable assembly may be a standalone device. Nevertheless, the rotating carousel (if used) is rotated to place each traceable filter in the optical path, thereby obtaining the real detector responses ("R2"). The R2 responses may be acquired any time after the optical computing device has been fabricated and assembled into a sensor.

After the real and simulated detector responses have been acquired, the calibration system then generates a mapping function which maps R1 and R2, channel by channel. In one illustrative method, a univariate mapping function is generated which maps each individual optical channel, as defined by the following mapping function:

$$R_{1,i} = R_{2,i} * \beta_i + \alpha_i \quad \text{Eq.(4)},$$

where $R_{1,i}$ is the simulated detector responses of the set of traceable optical filters on optical channel i; $R_{2,i}$ is the real detector response of the set of traceable optical filters on optical channel i; $\alpha_i$ is the offset of calibration line for channel i and $\beta_i$ is slope of calibration line for channel i. FIG. 3 shows a mapping function, $R_{1,}=R_2*\beta+\alpha$ [and corresponding plot useful to illustrative the mapping principle. In the shown example, three traceable filters are used to obtain the simulated R1 detector responses and the real R2 detector responses. In an alternative method, a multivariate mapping function may be generated which maps multiple optical channels to one optical channel, as defined by the following mapping function:

$$R_1 = R_2 * F \quad \text{Eq.(5)},$$

where F is a nonlinear or liner multivariate mapping function.

Thereafter, with reference back to FIG. 2, the reference spectra are used to calibrate optical computing device using the mapping function at block 204. Here, once the mapping function F has been determined, the real detector responses (spectra) of fluid samples can be calibrated to the simulated detector responses through the mapping function. Then the multivariate calibration model originally developed in step 1 above is applied on the calibrated detector responses to obtain the sample characteristic of interest/predict the concentration of the analyte of interest.

Figure 4:
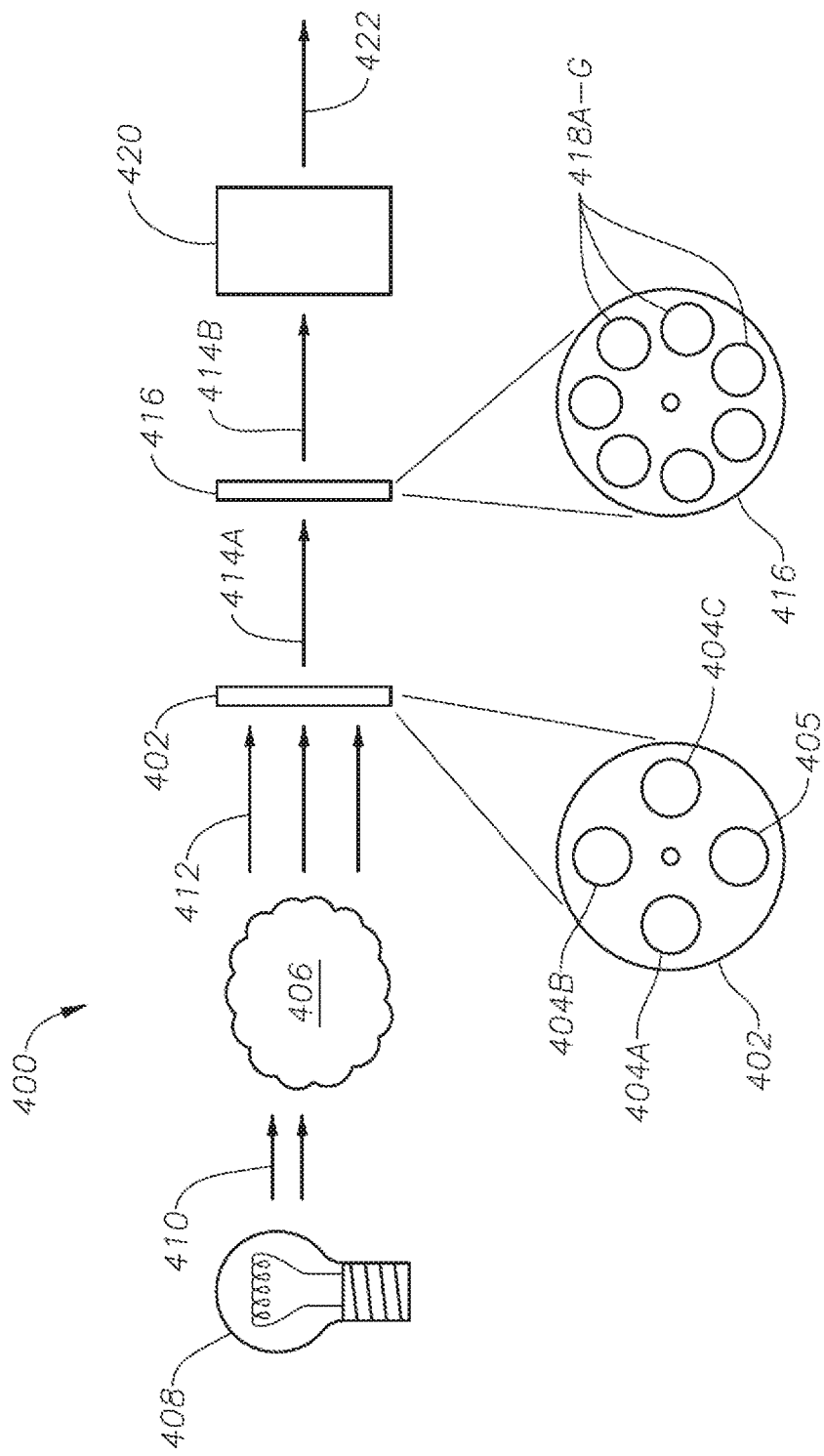
FIG. 4 is a block diagram of a self-calibrating optical computing device 400 used to interrogate a sample, according to certain illustrative embodiments of the present disclosure.

FIG. 4 illustrates a block diagram of a self-calibrating optical computing device 400 used to interrogate a sample, according to certain illustrative embodiments of the present disclosure. An electromagnetic radiation source 408 may be configured to emit or otherwise generate electromagnetic radiation 410. As understood in the art, electromagnetic radiation source 408 may be any device capable of emitting or generating electromagnetic radiation. For example, electromagnetic radiation source 408 may be a light bulb, light emitting device, laser, blackbody, photonic crystal, or X-Ray source, etc. In one embodiment, electromagnetic radiation 410 may be configured to optically interact with the sample 406 (wellbore fluid flowing through a wellbore or a portion of the formation, for example) and generate sample-interacted light 412. Sample 406 may be any fluid (liquid or gas), solid substance or material such as, for example, downhole tool components, tubulars, rock formations, slurries, sands, muds, drill cuttings, concrete, other solid surfaces, etc. In other embodiments, however, sample 406 is a multiphase wellbore fluid (comprising oil, gas, water, solids, for example) consisting of a variety of fluid characteristics such as, for example, elemental corrosive by-products, elements generated by sample material loss, C1-C4 and higher hydrocarbons, groupings of such elements, and saline water.

Sample 406 may be provided to optical computing device 400 through a flow pipe or sample cell, for example, containing sample 406, whereby it is introduced to electromagnetic radiation 410. While FIG. 4 shows electromagnetic radiation 410 as passing through or incident upon the sample 406 to produce sample-interacted light 412, it is also contemplated herein to reflect electromagnetic radiation 410 off of the sample 406 (i.e., reflectance mode), such as in the case of a sample 406 that is translucent, opaque, or solid, and equally generate the sample-interacted light 412.

After being illuminated with electromagnetic radiation 410, sample 406 containing an analyte of interest (a characteristic of the sample, for example) produces an output of electromagnetic radiation (sample-interacted light 412, for example). As previously described, sample-interacted light 412 also contains spectral patterns that reflect characteristics (e.g., density or composition) of the sample. Ultimately, processing circuitry, on board device 400 or remote therefrom, analyzes this spectral information to determine sample characteristics. Although not specifically shown, one or more spectral elements may be employed in optical computing device 400 in order to restrict the optical wavelengths and/or bandwidths of the system and, thereby, eliminate unwanted electromagnetic radiation existing in wavelength regions that have no importance. Such spectral elements can be located anywhere along the optical train, but are typically employed directly after the light source which provides the initial electromagnetic radiation.

In this illustrative embodiment, optical computing device 400 includes a first movable assembly 402 having at least two traceable optical filters ICE structures 404. In this example, three traceable filters 404A, B, and C are shown, along with an open hole 405. As illustrated, the movable assembly 402 may be characterized at least in one embodiment as a linear array or rotating disc, such as, for example, a chopper wheel, wherein traceable filters 404A-C and open hole 405 are radially disposed for rotation therewith. FIG. 4 also illustrates corresponding frontal views of the moveable assembly 402, which is described in more detail below. In other embodiments, however, movable assembly 402 may be characterized as any type of movable assembly configured to sequentially align at least one detector with the two or more traceable filters 404 or open hole 405.

During normal operation of optical computing device 400, moveable assembly 402 is rotated to positioned open hole 405 in the path of sample-interacted light 412 so that sample characteristics may be determined. However, as described in more detail below, when optical computing device 400 requires calibration, sample 406 is removed (e.g., fluid flow is prevented from sample cell, etc.) and moveable assembly 402 is rotated to position traceable filters 404A-C in the path of electromagnetic radiation 410.

Nevertheless, regardless of the position of moveable assembly 402, first optically-interacted light 414A is produced by the interaction of traceable filters 404A-C (or open hole 405) with sample-interacted light 412 (if open hole 405 is used) or electromagnetic radiation 410 (if filters 404A-C are used). A second moveable assembly 416 is positioned to optically interact with first optically-interactive light 414. Second moveable assembly 416 includes one or more optical elements such as, for example, ICE structures, narrow band filters, NDs, blockers, etc. which are positioned to interact as desired in order to produce second optically-interacted light 414B which corresponds to one or more characteristics of sample 406.

In certain exemplary embodiments, rotating disc 402 and 416 may be rotated at a desired frequency such that the desired optical element on disc 402 is aligned with the desired optical element on disc 416. Detector 420 then receives each second optically-interacted light 414B thereby generates an output signal 422. Accordingly, a signal processor (not shown) communicatively coupled to detector 420 processes all output signals in order to accomplish the calibration and/or sample characteristic determination operations of the present disclosure.

As described above, during normal operation of optical computing device 400, rotating disc 402 is rotated such that open hole 405 is positioned in the optical path of sample-interacted light 412 so that the desired characteristic of interest can be detected. However, when calibration of optical computing device 400 is needed, rotating disc 402 is rotated such that traceable filter 404A is positioned in the path of electromagnetic radiation 410 (sample 406 is removed in order to conduct the calibration), and the processor rotates discs 416 through all optical elements 418A-G, whereby second optically-interacted lights 414B are generated and detected by detector 420 accordingly. Then traceable filter 404B is positioned on the optical path, and optical elements 418A-G are rotated through again, and so on until all the real detector responses are acquired. Then, the simulated detector responses (acquired using the reference spectra of the traceable filters) are mapped to the real detector responses, whereby calibration of the real responses is achieved. Thereafter, sample 406 and open hole 405 are positioned in the optical path, and optical computing device 400 continues normal operation in its calibrated state.

Those ordinarily skilled in the art having the benefit of this disclosure realize the aforementioned optical computing device is illustrative in nature, and that there are a variety of other optical configurations which may be used. These optical configurations not only include the reflection, absorption or transmission methods described herein, but can also involve scattering (Raleigh & Raman, for example) as well as emission (fluorescence, X-ray excitation, etc., for example). In addition, the optical computing devices may comprise a parallel processing configuration whereby the sample-interacted light is split into multiple beams.

The illustrative embodiments and associated methods of the optical computing devices described herein may be used in a variety of environments. Such environments may include, for example, downhole well or completion applications. Other environments may include those as diverse as those associated with surface and undersea monitoring, satellite or drone surveillance, pipeline monitoring, or even sensors transiting a body cavity such as a digestive tract. Within those environments, the computing devices and temperature sensors are used to detect/monitor various sample characteristics within the environment.

Figure 5A:
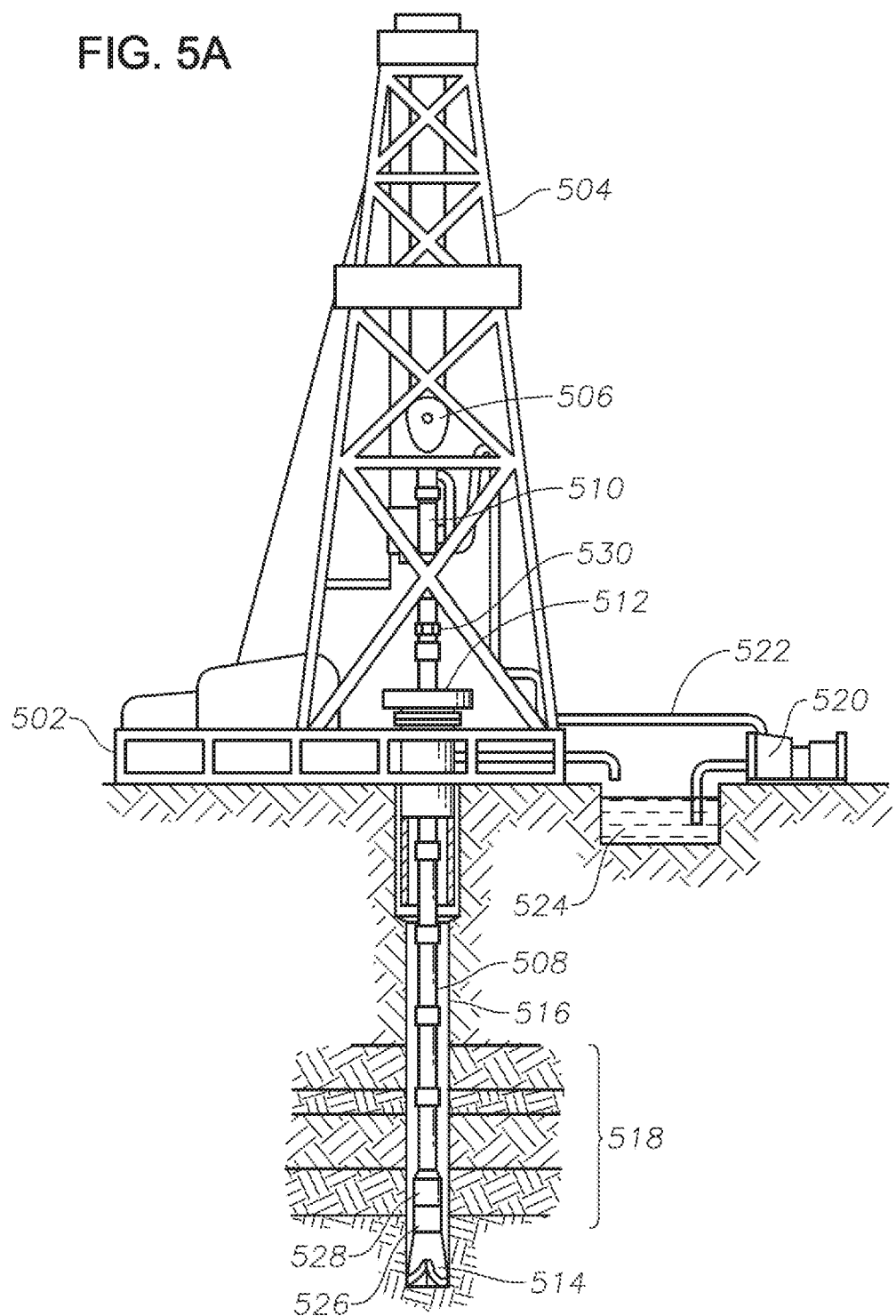
FIGS. 5A and 5B illustrate a self-calibrating optical computing device as described herein used in a logging-while-drilling ("LWD") application and wireline application, respectively, according to certain illustrative applications of the present disclosure.

FIG. 5A illustrates a self-calibrating optical computing device as described herein used in a logging-while-drilling ("LWD") application. FIG. 5A illustrates a drilling platform 502 equipped with a derrick 504 that supports a hoist 506 for raising and lowering a drill string 508. Hoist 506 suspends a top drive 510 suitable for rotating drill string 508 and lowering it through well head 512. Connected to the lower end of drill string 508 is a drill bit 514. As drill bit 514 rotates, it creates a wellbore 516 that passes through various layers of a formation 518. A pump 520 circulates 505 drilling fluid through supply pipe 522 to top drive 510, down through the interior of drill string 508, through orifices in drill bit 514, back to the surface via the annulus around drill string 508, and into a retention pit 524. The drilling fluid transports cuttings from the borehole into pit 524 and aids in maintaining the integrity of wellbore 516. Various materials can be used for drilling fluid, 510 including, but not limited to, a salt-water based conductive mud.

A reservoir interrogation system 526 (e.g., optical computing device) is integrated into the bottom-hole assembly near the bit 514. In this illustrative embodiment, reservoir interrogation system 526 is an LWD tool; however, in other illustrative embodiments, reservoir interrogation system 526 may be used in a wireline or tubing-conveyed logging application. Nevertheless, as drill bit 514 extends wellbore 516 through formations 518, reservoir interrogation system 526 collects data related to sample characteristics as described herein. In certain embodiments, reservoir interrogation system 526 may take the form of a drill collar, i.e., a thick-walled tubular that provides weight and rigidity to aid the drilling process. A telemetry sub 528 may be included to transfer images and measurement data/signals to a surface receiver 530 and to receive commands from the surface. In some embodiments, telemetry sub 528 does not communicate with the surface, but rather stores data for later retrieval at the surface when the logging assembly is recovered.

Still referring to FIG. 5A, reservoir interrogation system 526 includes a system control center (not shown), along with necessary processing/storage/communication circuitry, that is used to acquire sample characteristic and/or temperature measurement signals, as well as perform the calibration techniques described herein. In certain embodiments, once the measurement signals are acquired, the system control center calibrates the measurement signals and communicates the data back uphole and/or to other assembly components via telemetry sub 528. In an alternate embodiment, the system control center may be located at a remote location away from reservoir interrogation system 526, such as the surface or in a different borehole, and performs the processing accordingly.

Figure 5B:
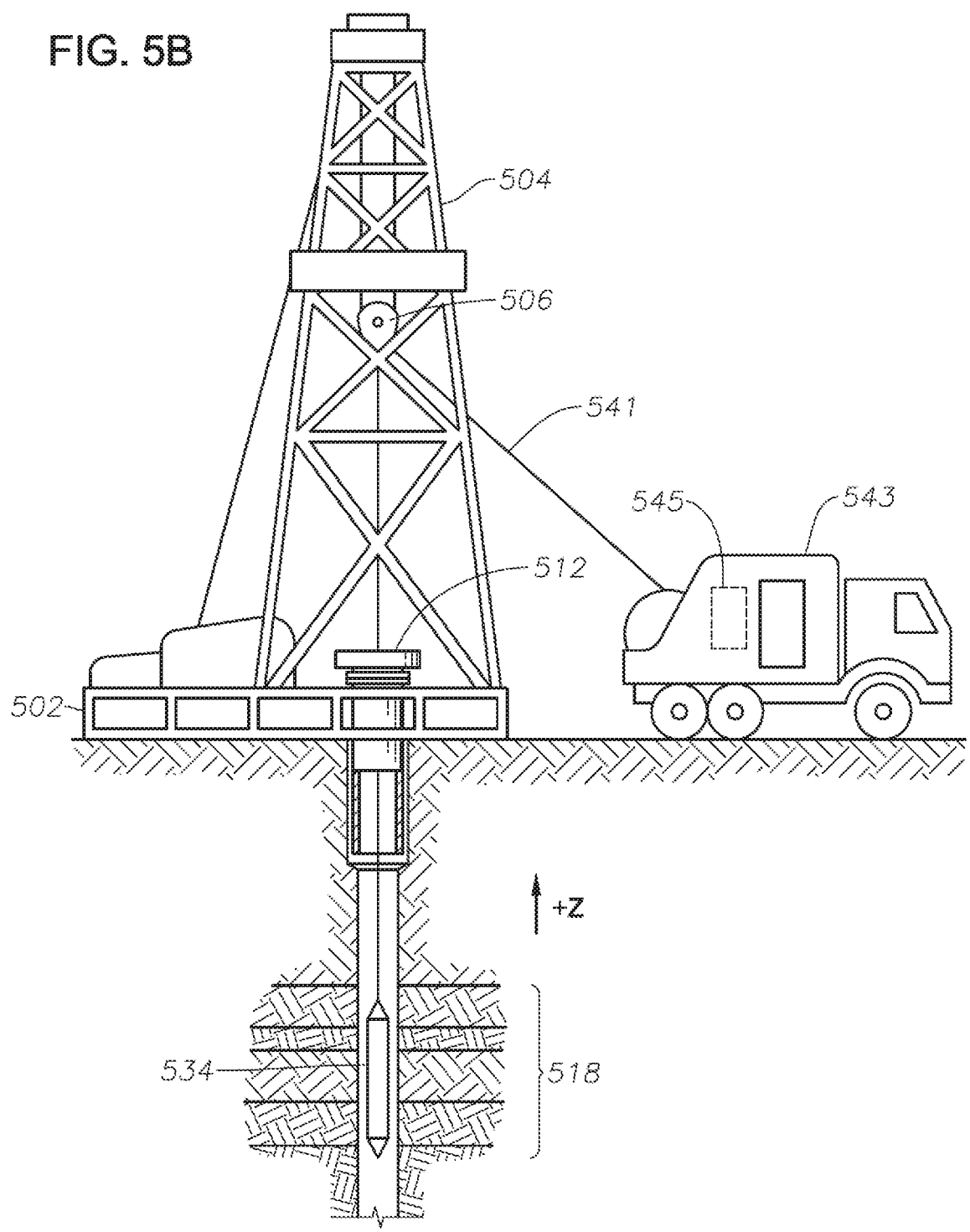

FIG. 5B illustrates an alternative embodiment of the present disclosure whereby a self-calibrating optical computing device as described herein is deployed in a wireline application. At various times during the drilling process, drill string 508 may be removed from the borehole as shown in FIG. 5B. Once drill string 508 has been removed, logging operations can be conducted using a wireline logging sonde 534, i.e., a probe suspended by a cable 541 having conductors for transporting power to the sonde and telemetry from the sonde to the surface (forming part of the reservoir interrogation system). Wireline sonde 534 may comprise an optical computing device, as described herein. A wireline logging sonde 534 may have pads and/or centralizing springs to maintain the tool near the axis of the borehole as the tool is pulled uphole. Logging sonde 534 can include a variety of other sensors including tools for measuring formation resistivity. A logging facility 543 collects sample characteristic measurements from the logging sonde 534, and includes a computer system 545 for processing and storing the measurements gathered by the sensors.

Accordingly, in both embodiments of FIGS. 5A and 5B, calibration of the optical computing device is performed downhole using traceable filters forming part of the computing device itself. However, in an alternate embodiment, the optical computing device may be calibrated using traceable filters external to the computing device.

In an alternative embodiment of the present disclosure, in addition to being used as calibration standards, the traceable filters can also be used as in-line optical filters to dynamically adjust the light levels for different optically dense fluids. For example, prior art optical devices currently use a weaker light level to drive the light source at 1.5 W because any more power saturates the detector for the most transparent fluids. As a result, darker fluids cannot always be measured since the light signal is too weak.

Accordingly, with reference to FIG. 4, in certain embodiments of the present disclosure, the traceable filters may be used to govern the intensity of the electromagnetic radiation generated by the light source. Here, a stronger light intensity is used for electromagnetic radiation source 408 (e.g., 15 W) and a traceable filter (e.g., allowing 10% transmission) is placed in line with the electromagnetic radiation. Accordingly, when a more transparent sample 406 is being analyzed, disc 402 is rotated to the 10% traceable filter to attenuate the light such that the detector will not become saturated. However, when a more optically dense sample fluid (opaque fluid, e.g.) is being analyzed, disc 402 may be rotated to another traceable filter which allows 70% transmission, for example, whereby the signal is strong enough to obtain a useable measurement. Any number of traceable filters with differing transmission levels may be used. Therefore, such an application provides a broader dynamic range for the optical computing device.

Accordingly, the illustrative methods and embodiments described herein provide a number of advantages. First, for example, instead of using real fluid samples as the calibration set, which is operationally expensive, posts safety hazard, and requires a designated facility to conduct the calibration testing, this disclosure uses a set of built-in traceable optical filter standards that allow the calibration process to be conducted safely anywhere and anytime with minimal operational cost. Second, due to the high stability and reproducibility of the traceable optical filters, the calibration is more accurate and precise than using fluid samples. Third, because the traceable filter disc can be built into the optical computing device configuration, the device can be calibrated downhole prior to measuring the real downhole sampling fluids. Fourth, because the calibration process can be conducted easily, the same computing device can be calibrated before measuring each sample to thereby reduce the risk of thermal drift.

Fifth, since calibration can be done in the tool directly, instead of in the sensor, the potential disparity between sensor and tool can be eliminated. Here, "sensor" refers to the standalone sensor package prior to assembly into a tool. When the sensor is assembled into a tool and shares electronic and control systems with other tool modules, it may cause the sensor response to change slightly when compared with standalone sensor Sixth, instead of developing a calibration model based upon real sample spectral data of each individual detector, which is cost prohibitive, the disclosed methods use a detector calibration approach that allows the calibration to be built based upon simulated spectral data of real fluids whose spectra were collected in one centralized lab.

Methods and embodiments described herein further relate to any one or more of the following paragraphs:

1. A method, comprising obtaining reference spectra of two or more optical filters, wherein the optical filters have different transmission levels and the reference spectra each have defined spectral patterns that simulate spectral data of a sample; and using the reference spectra to calibrate an optical computing device.

2. A method as defined in paragraph 1, wherein obtaining the reference spectra comprises obtaining the reference spectra using a laboratory spectroscopic instrument.

3. A method as defined in paragraphs 1 or 2, wherein obtaining the reference spectra further comprises using the reference spectra to generate a mapping function which calibrates measurements of the optical computing device.

4. A method as defined in any of paragraphs 1-3, wherein the reference spectra are used to generate a univariate mapping function.

5. A method as defined in any of paragraphs 1-4, wherein the reference spectra are used to generate a multivariate mapping function.

6. A method as defined in any of paragraphs 1-5, wherein obtaining the reference spectra comprises using the reference spectra to simulate detector responses of the optical filters; and using the reference spectra to calibrate the optical computing device comprises: obtaining real detector responses of the optical filters; generating a mapping function which maps the simulated detector responses to the real detector responses; and using the mapping function to calibrate measurements of the optical computing device.

7. A method as defined in any of paragraphs 1-6, wherein obtaining the real detector responses comprises: optically interacting electromagnetic radiation the optical filters to produce first optically-interacted lights which correspond to the defined spectral patterns of the reference spectra; optically interacting the optically-interacted lights with one or more Integrated Computational Element ("ICE") structures to produce second optically-interacted lights which correspond to one or more characteristics of the sample; generating output signals that correspond to the second optically-interacted lights using a detector; and using the output signals to generate the real detector responses.

8. A method as defined in any of paragraphs 1-7, wherein the calibration is performed using optical filters external to the optical computing device.

9. A method as defined in any of paragraphs 1-8, wherein the calibration is performed using optical filters forming part of the optical computing device.

10. A method as defined in any of paragraphs 1-9, wherein the calibration comprises moving the optical filters into a path of electromagnetic radiation using a moveable assembly.

11. A method as defined in any of paragraphs 1-10, wherein the calibration further comprises removing a sample from the path of the electromagnetic radiation.

12. A method as defined in any of paragraphs 1-11, further comprising: after the calibration is performed, moving the optical filters out of the path of the electromagnetic radiation; optically interacting the electromagnetic radiation with a sample to produce sample-interacted light; optically interacting the sample-interacted light with an Integrated Computational Element ("ICE") structure to produce optically-interacted light which corresponds to a characteristic of the sample; generating an output signal that corresponds to the optically-interacted light using a detector; and using the output signal to determine the characteristic of the sample.

13. A method as defined in any of paragraphs 1-12, further comprising, after the calibration is performed, using the optical filters to govern an intensity of the electromagnetic radiation.

14. A method as defined in any of paragraphs 1-13, wherein the calibration is performed downhole.

15. An optical computing device, comprising: electromagnetic radiation which optically interacts with two or more optical filters to produce first optically-interacted lights having defined spectral patterns that simulate spectral data of a sample; one or more Integrated Computational Element ("ICE") structures positioned to optically interact with the first optically-interacted lights to produce second optically-interacted lights which correspond to one or more characteristics of the sample; and a detector positioned to detect the second optically-interacted lights and generate output signals used to calibrate the optical computing device.

16. An optical computing device as defined in paragraph 15, wherein the optical filters are configured to calibrate the optical computing device.

17. An optical computing device as defined in paragraphs 15 or 16, further comprising a moveable assembly upon which the optical filters are positioned.

18. An optical computing device as defined in any of paragraphs 15-17, wherein the moveable assembly is a rotating carousel or a linear array.

19. An optical computing device as defined in any of paragraphs 15-18, wherein the moveable assembly further comprises an open hole.

20. An optical computing device as defined in any of paragraphs 15-19, wherein the optical filters are neutral density filters or glass.

21. An optical computing device as defined in any of paragraphs 15-20, wherein the optical computing device forms part of a reservoir interrogation system.

Furthermore, the illustrative methods described herein may be implemented by a system comprising processing circuitry or a computer program product comprising instructions which, when executed by at least one processor, causes the processor to perform any of the method described herein.

Although various embodiments and methods have been shown and described, the disclosure is not limited to such embodiments and methods and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A method, comprising:
    obtaining reference spectra of two or more optical filters, wherein obtaining the reference spectra comprises using the reference spectra to simulate detector responses of the optical filters,
    wherein the optical filters have different transmission levels and the reference spectra each have defined spectral patterns that simulate spectral data of a sample; and
    using the reference spectra to calibrate an optical computing device, wherein using the reference spectra to calibrate the optical computing device comprises:
        obtaining real detector responses of the optical filters;
        generating a mapping function which maps the simulated detector responses to the real detector responses; and
        using the mapping function to calibrate measurements of the optical computing device.

2. The method as defined in claim 1, wherein obtaining the reference spectra comprises obtaining the reference spectra using a laboratory spectroscopic instrument.

3. The method as defined in claim 1, wherein the reference spectra are used to generate a univariate mapping function.

4. The method as defined in claim 1, wherein the reference spectra are used to generate a multivariate mapping function.

5. The method as defined in claim 1, wherein obtaining the real detector responses comprises:
    optically interacting electromagnetic radiation the optical filters to produce first optically-interacted lights which correspond to the defined spectral patterns of the reference spectra;
    optically interacting the optically-interacted lights with one or more Integrated Computational Element ("ICE") structures to produce second optically-interacted lights which correspond to one or more characteristics of the sample;
    generating output signals that correspond to the second optically-interacted lights using a detector; and
    using the output signals to generate the real detector responses.

6. The method as defined in claim 1, wherein the calibration is performed using optical filters external to the optical computing device.

7. The method as defined in claim 1, wherein the calibration is performed using optical filters forming part of the optical computing device.

8. The method as defined in claim 7, wherein the calibration comprises moving the optical filters into a path of electromagnetic radiation using a moveable assembly.

9. The method as defined in claim 8, wherein the calibration further comprises removing the sample from the path of the electromagnetic radiation.

10. The method as defined in claim 8, further comprising:
    after the calibration is performed, moving the optical filters out of the path of the electromagnetic radiation;
    optically interacting the electromagnetic radiation with the sample to produce sample-interacted light;
    optically interacting the sample-interacted light with an Integrated Computational Element ("ICE") structure to produce optically-interacted light which corresponds to a characteristic of the sample;
    generating an output signal that corresponds to the optically-interacted light using a detector; and using the output signal to determine the characteristic of the sample.

11. The method as defined in claim 8, further comprising, after the calibration is performed, using the optical filters to govern an intensity of the electromagnetic radiation.

12. The method as defined in claim 1, wherein the calibration is performed downhole.

13. An optical computing device, comprising:
   electromagnetic radiation which optically interacts with two or more optical filters to produce first optically-interacted lights having defined spectral patterns that simulate spectral data of a sample;
   one or more Integrated Computational Element ("ICE") structures positioned to optically interact with the first optically-interacted lights to produce second optically-interacted lights which correspond to one or more characteristics of the sample; and
   a detector positioned to detect the second optically-interacted lights and generate output signals used to calibrate the optical computing device.

14. The optical computing device as defined in claim 13, wherein the optical filters are configured to calibrate the optical computing device.

15. The optical computing device as defined in claim 13, further comprising a moveable assembly upon which the optical filters are positioned.

16. The optical computing device as defined in claim 15, wherein the moveable assembly is a rotating carousel or a linear array.

17. The optical computing device as defined in claim 15, wherein the moveable assembly further comprises an open hole.

18. The optical computing device as defined in claim 13, wherein the optical filters are neutral density filters or glass.

19. The optical computing device as defined in claim 13, wherein the optical computing device forms part of a reservoir interrogation system.

20. An optical computing method, comprising:
   optically interacting electromagnetic radiation with two or more optical filters to produce first optically-interacted lights having defined spectral patterns that simulate spectral data of a sample;
   optically interacting one or more Integrated Computational Element ("ICE") structures with the first optically-interacted lights to produce second optically-interacted lights which correspond to one or more characteristics of the sample; and
   using a detector to detect the second optically-interacted lights and generate output signals used to calibrate the optical computing device.

21. The method as defined in claim 20, further comprising calibrating the optical computing device using the optical filters.

22. The method as defined in claim 21, wherein the calibration is performed using optical filters external to the optical computing device.

23. The method as defined in claim 21, wherein the calibration is performed using optical filters forming part of the optical computing device.

24. The method as defined in claim 21, wherein the calibration comprises moving the optical filters into a path of electromagnetic radiation using a moveable assembly.

25. The method as defined in claim 24, wherein the calibration further comprises removing the sample from the path of the electromagnetic radiation.

26. The method as defined in claim 20, wherein the calibration is performed downhole.

* * * * *